(12) United States Patent
Brown et al.

(10) Patent No.: US 7,504,546 B2
(45) Date of Patent: Mar. 17, 2009

(54) APPARATUS AND METHOD FOR THE REMOVAL OF WATER FROM ETHANOL

(76) Inventors: Christopher J. Brown, 64 Mt. Vernon Rd., Amherst, NY (US) 14223; Vladimir Hlavacek, 4921 E. Pineledge Dr., Clarence, NY (US) 14031; Marian Simo, 4 Holly La., Apt. 8, Tonawanda, NY (US) 14150

( * ) Notice: Subject to any disclaimer, the term of this patent is extended or adjusted under 35 U.S.C. 154(b) by 3 days.

(21) Appl. No.: 11/771,553

(22) Filed: Jun. 29, 2007

(65) Prior Publication Data

US 2008/0039665 A1 Feb. 14, 2008

Related U.S. Application Data

(60) Provisional application No. 60/806,278, filed on Jun. 30, 2006.

(51) Int. Cl.
*C07C 29/74* (2006.01)
*C07C 29/76* (2006.01)
(52) U.S. Cl. .................. 568/917; 586/917; 586/916
(58) Field of Classification Search ............. 568/917, 568/916
See application file for complete search history.

(56) References Cited

U.S. PATENT DOCUMENTS 4,465,875 A * 8/1984 Greenbank et al.
4,964,888 A * 10/1990 Miller

* cited by examiner

*Primary Examiner*—Elvis O Price
(74) *Attorney, Agent, or Firm*—Paul T. Lavole; Jaeckle, Fleischman & Mugel, LLP

(57) ABSTRACT

An apparatus and method for drying ethanol includes a first reaction chamber for carrying out the removal of water from wet ethanol, a feed inlet for introducing the wet ethanol into the reaction chamber, a product outlet for removing dry ethanol from the reaction chamber, an optional fuel inlet for introducing a fuel into the reaction chamber, and a particulate bed, including sorbent particles, that is disposed within the reaction chamber. In a preferred embodiment, the bed is divided into first and second zones each provided with different size sorbent particles. In another preferred embodiment, the bed contains a mixture of sorbent particles and catalyst particles. The sorbent particles operate to remove water from the wet ethanol and form hydrated-sorbent particles. The catalyst particles operate to promote chemical reaction of the fuel, generating heat that causes removal of water from the hydrated-sorbent particles and regenerating the sorbent particles.

21 Claims, 4 Drawing Sheets

APPARATUS AND METHOD FOR THE REMOVAL OF WATER FROM ETHANOL

CROSS-REFERENCE TO RELATED APPLICATION

This application claims priority to U.S. Provisional Application No. 60/806,278, filed Jun. 30, 2006.

FIELD OF THE INVENTION

This invention generally relates to the removal of water from ethanol by a sorbent material and regeneration of the sorbent material.

BACKGROUND OF THE INVENTION

Decreasing world reserves and diminishing availability of crude oil have created considerable incentive for the development and use of alternative fuels. In recent years the ever increasing value of fossil hydrocarbon liquids and gases has directed research and development to the possibilities of employing bio-mass materials for fuel purposes. In particular, attention has been focused on fermentation derived ethanol for car fuel purposes. Ethanol is gaining wide popularity as such a fuel when mixed with gasoline to form a mixture known as gasohol. Automobiles can run on gasohol containing up to about 10 volume percent ethanol without requiring engine modifications. To prevent phase separation during storage, gasohol should contain at most only small amounts of water. Thus the ethanol that is mixed with the gasoline needs to be relatively dry. Desirably dry ethanol contains 1% or less by weight of water, preferably less than 0.5% water, and more preferably 0.3% or less of water.

One common method of ethanol production is the fermentation of mash, usually from corn and/or sugar cane. During alcoholic fermentation, sugar, particularly glucose, is converted into ethanol and carbon dioxide in the presence of yeast cells that contain the enzyme complex zymase. Glucose is produced by enzymatic splitting of maltose, which is itself formed during the hydrolytic, enzymatic splitting of starch or is developed during the manufacture of sugar. In addition to ethanol, the ethanol solutions developed during alcoholic fermentation contain soluble and insoluble components of vegetable cells and builders, yeast cells, starch and fractions of starch, various sugars, salts, and water. The ethanol content of the solutions obtained during alcoholic fermentation is usually about 6 wt. % and about 94% water. At higher alcohol levels, the bacteria begin to die and fermentation slows or ceases.

As described in the online *Encyclopaedia Brittanica*, rectification is the process of purifying alcohol by repeatedly or fractionally distilling it to remove water and undesirable compounds. A fermentation mixture primarily contains water and ethanol, and distillation involves increasing the percentage of ethanol in the mixture. Water vaporizes very easily, however, and, unless care is taken, the distillate of a fermentation mixture will contain unacceptably large quantities of water. The fermentation mixture furthermore contains small quantities of constituents such as, for example, organic aldehydes, acids, esters, and higher alcohols. The ones that remain in the product are called congeners, and the congener level is controlled by the particular rectification system and by the system's method of operation.

A multicolumn rectifying system commonly consists of three to five columns. The first column is a preliminary separation column called the beer still, or analyzer. It usually consists of a series of metal plates with holes punched in them and baffles to control the liquid levels on the plates. The product coming from this column is generally between 55 and 80 percent ethanol. A 95-percent product can be produced on a two-column system consisting of a beer column and a rectifying column.

Water cannot be completely removed from ethanol by distillation because of the formation of an azeotrope containing 95.5 wt. % ethanol and 4.5 wt. % water, which limits the upper concentration of ethanol that can be obtained by rectification regardless of the number of theoretical plates employed. Distillation processes have the further drawback that they require a large amount of energy. Special techniques are required to dehydrate ethanol beyond the 95.5 wt. % ethanol content level and typically require a considerable additional amount of energy. The high energy cost of ethanol separation by distillation is an economic impediment for using ethanol produced by alcoholic fermentation as an engine fuel.

Ethanol can also be produced by the catalytic hydration of ethylene. This reaction is often carried out in the presence of excess water with a catalyst such as phosphoric acid on clay. The resulting ethanol is not free of water.

Thus, although wet ethanol can be readily produced, new methods and apparatus are needed in order to economically separate water from ethanol. Wet ethanol refers to ethanol that contains water. Typically wet ethanol contains water in the range of 1% to 95% by weight, often in the range of about 2% to 50%, commonly in the range of about 3% to 30%, and frequently in the range of 4°/, to 10% by weight.

Pressure swing adsorption (PSA) is a gas separation process in which the adsorbent is regenerated by rapidly reducing the partial pressure of the adsorbed component, either by lowering the total pressure or by using a purge gas. In the original PSA cycles, invented by Skarstrom (1960), the two steps of adsorption and depressurization/purge are carried out in two adsorbent beds operated in tandem, enabling the processing of a continuous feed. Since introduction of the Skarstrom cycle, many more sophisticated PSA processes have been developed and commercialized. Such processes have attracted increasing interest more recently because of their low energy requirements and low capital investment costs.

The selectivity in a PSA process comes from differences in either adsorption equilibrium (equilibrium-controlled) or adsorption rate (kinetic-controlled) between the components to be separated. Although the overall performance of PSA depends on both equilibrium and kinetics, the relative importance varies for different applications (Ruthven et al., 1994). PSA is best suited for components that are not too strongly adsorbed. On the other hand, thermal swing adsorption (TSA) is preferred for very strongly adsorbed components, since a modest change of temperature produces a large change in gas-solid adsorption equilibrium. With better understanding of adsorbents and advances in their development for more efficient separation, there are many economic incentives for the further design and improvement of adsorption processes for gas separation.

In a PSA system, regeneration is achieved by first stopping the feed flow, then depressurizing the adsorbent, usually by passing regeneration gas through the bed counter-current to the feed direction. The regenerating gas is generally at a lower pressure than that of the air and is free of impurities. During the feed step, the adsorption process generates heat, which causes a thermal pulse to progress downstream through the bed. During the regeneration process, this same amount of heat must be supplied to desorb the impurities that have been adsorbed. In PSA, the aim is to commence regeneration before the heat pulse mentioned above has reached the downstream end of the bed. The direction of the heat pulse is reversed by the regeneration process, and the heat derived from the adsorption stage is then used for desorbing the impurities during regeneration, thereby avoiding the need to add heat during the regeneration step.

In the TSA process, the cycle time is extended, and the heat pulse is allowed to exit the adsorbent bed during the feed period. To achieve regeneration, it is therefore necessary to supply heat to desorb the material. To this end, the regenerating gas is heated for a period of time to produce a heat pulse that moves through the bed counter-current to the feed direction. This flow of heated regenerating gas is usually followed by a flow of cool regenerating gas that continues the displacement of the heat pulse through the bed toward the upstream end.

Each process has its own characteristic advantages and disadvantages. TSA is energy intensive because of the need to supply heat to the regenerating gas. Typically, there will be more than one unwanted gas component removed in the process, and generally one or more of these components will adsorb strongly and others much more weakly. The temperature used for regeneration in TSA needs to be sufficient for the desorption of the more strongly adsorbed component. The temperatures required for the regenerating gas are typically high enough, e.g., 150-200° C., to place demands on the system engineering which increases costs.

While the PSA system avoids many of the disadvantages associated with high temperatures, the short cycle time that characterizes PSA has its own consequences. In each cycle of operation, the adsorbent is subjected to a feed period during which adsorption takes place, followed by depressurization, regeneration and repressurization. During depressurization, the feed gas in the bed is vented off and lost, which is referred to as a "switch loss." The short cycle time in the PSA system gives rise to high switch losses and, because the cycle is short, it is necessary that the repressurization be conducted quickly. This rapid repressurization causes transient variations in the feed and product flows, which can adversely affect the plant operation, particularly the operation of processes downstream from the adsorption system.

Derr, U.S. Pat. No. 2,137,605, the disclosure of which is incorporated herein by reference, describes a method of producing anhydrous and absolute alcohol that comprises passing alcohol vapors containing water vapor through a bed of freshly reactivated alumina moistened with liquid alcohol.

Oulman et al., U.S. Pat. No. 4,277,635, the disclosure of which is incorporated herein by reference, describes a process of concentrating relatively dilute aqueous solutions of ethanol by passage through a bed containing granules of crystalline silica polymorph such as silicate, which adsorb the ethanol. A displacer fluid containing at least 80 wt. % ethanol is continuously passed through the bed to displace residual dilute ethanol feed without displacing the ethanol from the granules, and then removing the adsorbed ethanol together with a portion of the displaces fluid.

Greenbank et al., U.S. Pat. No. 4,465,875 and Ginder, U.S. Pat. No. 4,407,662, the disclosures of which are incorporated herein by reference, describe the use of molecular sieves to dry ethanol.

Fornoff, U.S. Pat. No. 4,273,621, the disclosure of which is incorporated herein by reference, describes a process for dehydration of ethanol comprising distilling a crude aqueous ethanol feedstock to produce a gaseous ethanol-water mixture containing about 90 wt. % ethanol, drying the mixture in the presence of carbon dioxide with a crystalline zeolite 3A, and allowing the product ethanol to condense at ambient temperatures.

Umekawa, JP Appl. No. 59004415, the disclosure of which is incorporated herein by reference, teaches that the size of an air purification cylinder and the pressure drop within it can by reduced through the use in the adsorbent bed of a deep layer of large particles (3.2 mm), followed by a shallow layer of small particles (1.6 mm) of the same adsorbent. The bed size and pressure drop of this layered configuration are lower than for beds constructed solely of 3.2 mm or of 1.6 mm particles.

Miller, U.S. Pat. No. 4,964,888, the disclosure of which is incorporated herein by reference, describes a multiple zone adsorption process using larger particles in the equilibrium zone and smaller particles in the mass transfer zone (MTZ), which reduces the size of the MTZ and minimizes the pressure drop increase that would occur if only small particles were used in both zones. The process is applicable to the separation of hydrogen from a feed containing hydrogen and at least one other component selected from among carbon monoxide, methane, and nitrogen.

Garrett, UK Pat. Appl. GB 2 300 577, the disclosure of which is incorporated herein by reference, describes an adsorption apparatus suitable for the separation of nitrogen from a stream of compressed air that contains particles in the size range between 6 mesh and 12 mesh, which are deployed either in discrete layers or as a gradient of sizes, the largest particles being located near the feed inlet, and the smallest particles downstream near the outlet of the adsorber.

Batta, U.S. Pat. No. 3,564,816, the disclosure of which is incorporated herein by reference, describes a pressure swing process using at least four adsorption zones to separate, for example, $CO$, $CO_2$, $CH_4$, $NH_3$, $H_2S$, $A$, $N_2$, and $H_2O$ from $H_2$, and $O_2$, $N_2$, and $CO_2$ from air.

Jones et al., U.S. Pat. No. 4,194,892, the disclosure of which is incorporated herein by reference, describes a rapid adiabatic pressure swing process useful for separating nitrogen from air, ethylene from nitrogen, and methane and/or carbon monoxide from hydrogen, the total cycle time being less than 30 seconds.

Reiss, U.S. Pat. No. 5,114,440, the disclosure of which is incorporated herein by reference, describes a process for oxygen enrichment of air by means of vacuum swing adsorption using adsorbers containing Ca zeolite A molecular sieves, the adsorbers of the VSA units being filled with separate layers of Ca xeolite A molecular sieves having different adsorption characteristics.

Hay et al., U.S. Pat. No. 5,176,721, the disclosure of which is incorporated herein by reference, describes an adsorber apparatus that is preferably used for the separation of oxygen from air and comprises a vessel containing an adsorbent mass separated into two longitudinal parts, the first part containing smaller particles and the second part containing larger particles.

Bloch, U.S. Pat. No. 3,474,023, the disclosure of which is incorporated herein by reference, describes an apparatus for continuous drying of a moist fluid such as hexane that utilizes a low DC potential to electrolyze the water adsorbed by a desiccant such as anhydrous calcium sulfate, thereby producing gaseous hydrogen and oxygen that can be separately collected.

Jean, U.S. Pat. No. 3,359,707, the disclosure of which is incorporated herein by reference, describes a method and apparatus for removing carbon dioxide and moisture from stale air, wherein the adsorbent bed is regenerated using high frequency electrical energy to effect dielectric heating of the adsorbent particles.

Koseki et al, U.S. Pat. No. 4,205,459, the disclosure of which is incorporated herein by reference, describes an apparatus for regenerating an absorbent in which adsorbed water is removed by heating in a furnace.

Mezey at al., U.S. Pat. No. 4,322,394, the disclosure of which is incorporated herein by reference, describes the separation of a gas mixture by selective adsorption of, for example, carbon dioxide and hydrogen sulfide from natural gas, using microwave heating to remove the adsorbed materials from saturated solid noncarbon adsorbents. Park et al., U.S. Pat. No. 6,634,119, the disclosure of which is incorporated herein by reference, describes an adsorptive drying apparatus in which microwaves are applied during the regeneration of an adsorbent.

Bonnissel, Luo, and Tondeur, *Ind. Eng. Chem. Res.,* 2001, 40 (10), 2322-2334, 2001) describes a thermal swing adsorption process based on a composite adsorbent bed consisting of an arrangement of layers of activated carbon particles that are separated by sheets of a highly conductive graphite material. The process, which also makes use of thermoelectric devices (Peletier elements) to alternately heat and cool the adsorbent bed, is illustrated experimentally by the uptake and concentration of carbon dioxide from a helium flow.

Despite the technology described above, there remains a need to development new apparatus and methods to be able to economically separate water from ethanol on a large scale. In particular there is a need to produce ethanol that is nearly free of water.

SUMMARY OF THE INVENTION

The present invention is directed to an apparatus for drying ethanol that includes a first reaction chamber for carrying out the removal of water from wet ethanol, a feed inlet for introducing wet ethanol into the reaction chamber, a product outlet for removing dry ethanol from the reaction chamber, an optional gas inlet for introducing a gas into the reaction chamber, and a particulate bed that is disposed within the reaction chamber and comprises a mixture of sorbent particles.

In one aspect of the invention, the apparatus includes at least one second reaction chamber and at least one thermal-transfer chamber, wherein the thermal-transfer chamber is adjacent to both the first and second reaction chambers. In one embodiment, the thermal-transfer chamber is continuous to both the first and second reaction chambers. In another embodiment, the thermal-transfer chamber is contiguous to both the first and second reaction chambers. The thermal-transfer chamber has both an inlet for introducing a cooling or heating material and an outlet for removing said cooling or heating material.

In another aspect of the invention, the particulate bed includes both sorbent particles and catalyst particles. In a first phase of operation, wet ethanol enters the first reaction chamber and the sorbent particles operate to adsorb water from the wet ethanol. In a second phase of operation the dry ethanol is removed from the reaction chamber and a fuel enters the chamber. The catalyst particles promote a chemical reaction of the fuel resulting in generation of heat. The thermal energy generated by the reaction heats the hydrated-sorbent particles, causing removal of adsorbed water and thereby regenerating the sorbent particles.

The present invention is further directed to a process for drying ethanol that comprises introducing wet ethanol via a feed inlet into a first reaction chamber that contains a particulate bed comprising sorbent particles, and is further provided with a product outlet for removing dry ethanol. The particulate bed comprises a first zone proximate to the feed inlet and a second zone proximate to the product outlet, the sorbent particles in the first zone having an average particle size larger than the average particle size of the sorbent particles in the second zone. The process further comprises adsorbing water from the wet ethanol onto the sorbent particles, and removing dry ethanol from the reaction chamber via the product outlet.

DETAILED DESCRIPTION OF THE INVENTION

Figure 1:
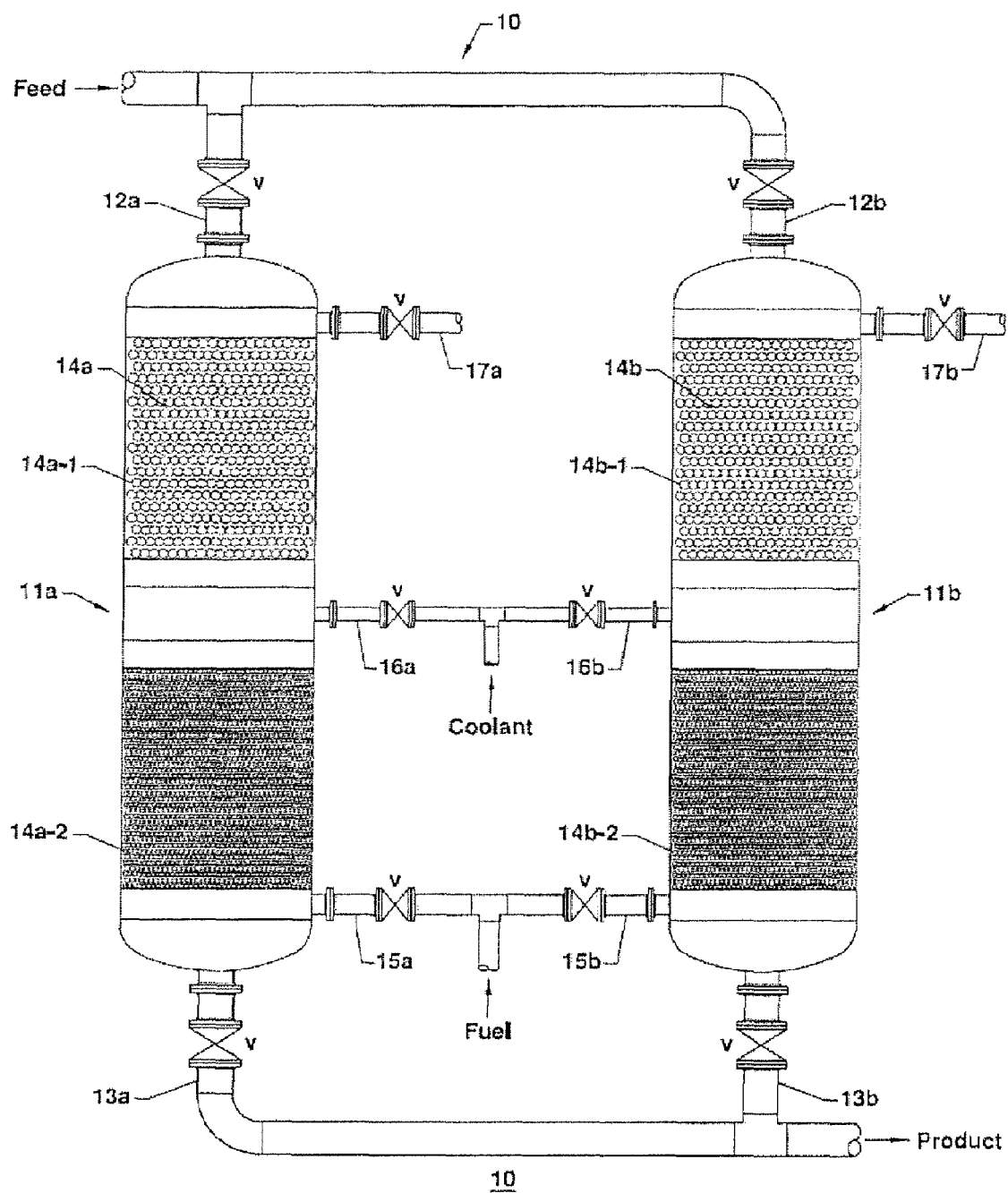
FIG. 1 schematically depicts an embodiment of the apparatus of the present invention that includes two reaction chambers.

One aspect of the present invention is directed toward an apparatus for drying ethanol. The apparatus includes a first reaction chamber for carrying out the removal of water from wet ethanol. The apparatus is provided with a feed inlet for introducing the wet ethanol into the reaction chamber, a product outlet for removing dry ethanol from the reaction chamber, an optional gas inlet for introducing a gas into the reaction chamber, and a particulate bed comprising sorbent particles disposed within the chamber.

Sorbent particles are particles that have the capacity to bind to water by the process of either absorption or adsorption or both. Sorbent particles included in the particulate bed preferably comprise alumina, silica, zeolite, and/or combinations thereof.

In one desirable embodiment, the sorbent particles include zeolites, which are inorganic porous material having a highly regular structure of pores and chambers that allow some molecules to pass through, and causes others to be excluded. The zeolites are silicates consisting of interlocking tetrahedrons of $SiO_4$ and $AlO_4$. Desirable zeolites have vacant spaces in their structures that allow space for water molecules to be incorporated but exclude larger molecules such as ethanol. The spaces are often interconnected and form long wide channels of varying sizes. Zeolites are characterized by their ability to lose and absorb water without damage to their crystal structures.

Useful sorbents also include materials that are frequently referred to as molecular sieves, which are synthetic zeolites. Molecular sieves having an average pore diameter of about 2.5 angstrom to about 3.5 angstrom are desirable. In particular, molecular sieves having a pore size of about 3 angstroms, often referred to as 3A molecular sieves, are especially useful. Another useful sorbent is activated alumina ($Al_2O_3$), which has a very high surface-area-to-weight ratio. In general it is a very porous material. It removes water by adsorption. The water reversibly binds to the alumina.

In one embodiment of the invention, the sorbent particles comprises a first zone proximate the feed inlet and a second zone proximate the product outlet, the sorbent in the first zone having an average particle size larger than the average particle size of the sorbent particles in the second zone. In one embodiment, the size of the particles in the first zone are in the range of about 0.15 to 0.75 cm and the size of the particles in the second zone are in the range of about 0.05 to 0.25 cm. In another suitable embodiment, the particles in the first zone are about twice as large as the particles in the second zone. In one desirable embodiment the sorbent particles in the first zone have an average particle size of approximately 0.32 cm (0.125 inch) diameter, and the sorbent particles in the second zone have an average particle size of approximately 0.16 cm (0.060 inch) diameter.

In a first phase of operation, wet ethanol enters the reaction chamber and the sorbent particles remove water from the wet ethanol. In a second phase of operation the dry ethanol is removed from the reaction chamber, for example, by depressurization of the chamber. In a third phase, a gas is introduced into the reaction chamber through the gas inlet valve. The gas removes the water from the hydrated-sorbent particles regenerating the sorbent. In a fourth phase, the gas containing water vapor is removed from the reaction chamber, followed by repressurzation.

In one embodiment the gas includes an inert purge gas, such as air or nitrogen. The gas is sufficiently warm so as to heat the hydrated-sorbent particles causing vaporization of the water associated with the particles. The resulting water vapor is removed form the reaction chamber along with the purge gas.

Following regeneration of the sorbent by heating, the sorbent preferably is cooled prior to the next adsorption step, preferably by injection of a fine spray of ethanol into the chamber, sometimes referred to as a "cold shot". The resulting vaporization of the ethanol cools the sorbent. Subsequently the ethanol vapor can be recovered by an external condenser. Alternatively, cooling can be achieved by injection of ethanol vapor that is produced by a distillation column.

In another desirable embodiment, the particulate bed comprises a heterogeneous mixture of sorbent particles and catalyst particles. Desirably, the sorbent particles and the catalyst particles are about the same geometrical size and shape. The mixture of sorbent particles and catalyst particles in the particulate bed preferably comprise a weight ratio of sorbent to catalyst of about 10:1 to about 30:1.

Alternatively, some or all of the sorbent particles may be modified to contain the catalyst, for example, platinum metal. For instance, catalyst may be deposited on the surface of the sorbent particle. In this case, the modified sorbent particles function to both take up water in one phase of operation and to catalyze a chemical reaction in a subsequent phase.

When a catalyst is present, the first and second phase of operation are as described above. In the third phase of operation, fuel is allowed to enter the chamber through the gas inlet valve. The catalyst particles promote a chemical reaction of the fuel, resulting in generation of heat. The thermal energy generated by the reaction heats the hydrated-sorbent particles, causing removal of adsorbed water and thereby regenerating the sorbent particles. In a fourth phase, the water vapor produced is removed from the reaction chamber, either by depressurization or by means of a purge gas, and the warm sorbent particles are cooled as described above.

The catalyst particles comprising the particulate bed may be an oxidation catalyst, a low-temperature water-gas shift catalyst or a combination thereof. A preferred oxidation catalyst is platinum-activated alumina.

Other preferred catalysts are described in U.S. Pat. No. 6,387,554, the disclosure of which is incorporated herein by reference. An example of a catalyzed oxidation reaction involves reaction of ethanol with water and oxygen to form hydrogen gas and carbon dioxide (eq. 1). The reaction is exothermic, thus generating heat.

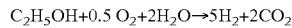

$$C_2H_5OH + 0.5\,O_2 + 2H_2O \rightarrow 5H_2 + 2CO_2 \qquad \text{(eq. 1)}$$

Water-gas shift catalysts are discussed in, for example, Cai et al., U.S. Pat. No. 6,627,572, the disclosure of which is incorporated herein by reference. Preferred water-gas shift catalysts include catalysts containing copper oxide, zinc oxide, aluminum oxide, and combinations thereof. An example of a catalyzed water-gas shift reaction involves the reaction of water and carbon monoxide to form hydrogen gas and carbon dioxide (eq. 2). This reaction is desirable because it consumes water and not ethanol.

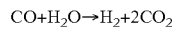

$$CO + H_2O \rightarrow H_2 + 2CO_2 \qquad \text{(eq. 2)}$$

Examples of useful fuels that undergo catalytic reaction to generate heat are carbon monoxide, butane or propane, all of which form carbon dioxide upon oxidation. Carbon monoxide is a preferred fuel because no water is farmed as a by-product, which results in greater thermal effectiveness. Because the heat provided by the fuel combustion is generated within the volume of the sorbent, very high rates of heat transfer are achievable. Thus, introduction of carbon monoxide into the reaction chamber in the presence of a water-shift catalyst included in the particulate bed results in an exothermic reaction that consumes water and produces carbon dioxide and hydrogen gas. The heat generated also produces water vapor. Thus, water is removed very effectively, both chemically and thermally, from the hydrated-sorbent, resulting in a highly activated sorbent.

In a further embodiment, a coolant inlet is provided for introducing into the reaction chamber a coolant that operates to cool the heated sorbent particles following removal of the adsorbed water from the hydrated-sorbent particles. The coolant preferably comprises a liquid, such as an alcohol, and preferably is ethanol. Desirably the liquid is injected into the reaction chamber as a fine spray.

In another further embodiment of the invention, the mixture of sorbent and catalyst particles comprise a first zone proximate the feed inlet and a second zone proximate the product outlet, the sorbent and catalyst particles in the first zone having an average particle size larger than the average particle size of the sorbent and catalyst particles in the second zone. Preferably, the sorbent and catalyst particles in the first zone are of approximately the same average particle size; similarly, the sorbent and catalyst particles in the second zone are also of approximately the same average particle size. Desirably the size of the particles in the first zone are in the range of about 0.15 to 0.75 cm and the particles in the second zone are in the range of about 0.05 to 0.25 cm. In one suitable embodiment the sorbent particles in the first zone have an average particle size of approximately 0.32 cm (0.1.25 inch) diameter, and the sorbent particles in the second zone have an average particle size of approximately 0.16 cm (0.060 inch) diameter.

In a still further embodiment of the invention, the apparatus includes a second reaction chamber. Wet ethanol is fed into the first chamber, and water is adsorbed by the particulate bed therein. The first chamber then undergoes depressurization, regeneration of the adsorbent, and repressurization. During this regeneration portion of the cycle in the first chamber, wet ethanol is fed into the second chamber and water is adsorbed on the particulate bed therein, following which the second chamber undergoes depressurization, regeneration of the adsorbent, and repressurization. In each of the chambers, depressurization is preferably accomplished by connection to a vacuum source. As described, regeneration of the sorbent in the particulate bed is achieved by introduction of a purge gas or more preferably by introduction of a heat-generating fuel that undergoes reaction in the chamber. The combination of a purge gas and a heat-generating fuel may also be advantageous. The thermal energy thus generated removes water from the sorbent.

FIG. 1 schematically depicts one embodiment of the current invention. The apparatus 10 includes two substantially similar reaction chambers 11a and 11b, each of which includes a feed inlet 12a and 12b, respectively, for the introduction of wet ethanol, and a product outlet 13a and 13b, respectively, for the removal of dry ethanol. Reaction chambers 11a and 11b each further include a particulate bed 14a and 14b, respectively, each of which preferably comprises a first zone 14a-1 and 14b-1, respectively, and a second zone, 14a-2 and 14b-2, respectively.

Particulate bed first zones 14a-1 and 14b-1, which are disposed proximate feed inlets 12a and 12b, respectively, each contain particles whose average size is larger than those contained in particulate bed second zones 14a-2 and 14b-2, which are disposed proximate product outlets 13a and 13b, respectively. Particulate bed first zones 14a-1 and 14b-1 and second zones 14a-2 and 14b-2 each preferably include a mixture of adsorbent particles and catalyst particles. The adsorbent and catalyst particles included within a particular zone are preferably of about the same size.

Reaction chambers 11a and 11b each further include a fuel inlet 15a and 15b, respectively, for the introduction of fuel to heat particulate beds 14a and 14b, respectively, and coolant inlets 16a and 16b, respectively, for the introduction of coolant to cool particulate beds 14a and 14b, respectively. Apparatus 10 also includes vents 17a and 17b for removal of gaseous by-products and valves V for regulating the various gas flows.

In a further embodiment, the apparatus includes a first and a second reaction chamber and one or more additional reaction chambers. The additional reaction chamber(s) function in the same manner as the first and second chambers previously described. Wet ethanol is fed into the chamber and water is removed by the particulate bed. The dry ethanol is removed and the sorbent is regenerated.

In another aspect of the invention, the inventive apparatus includes two or more reaction chambers each of which is tubular in shape and each chamber is separated from the adjacent chamber(s) by a thermal-transfer chamber. The reaction chamber is provided with a feed inlet for introducing wet ethanol, a product outlet for removing dry ethanol from the reaction chamber, an optional gas inlet for introducing a gas into the reaction chamber, and a particulate bed comprising sorbent particles disposed within the chamber. It is desirable for the tubular reaction chambers to be relatively narrow to ensure rapid heat transfer.

Each thermal-transfer chamber is equipped with an inlet valve and an exit value. A coolant material or a heating material may be introduced into the thermal-transfer chamber. The cooling material can remove heat from the adjacent reaction chambers by thermal transfer. The heating material can add heat to the adjacent reaction chambers also by thermal transfer.

Figure 2:
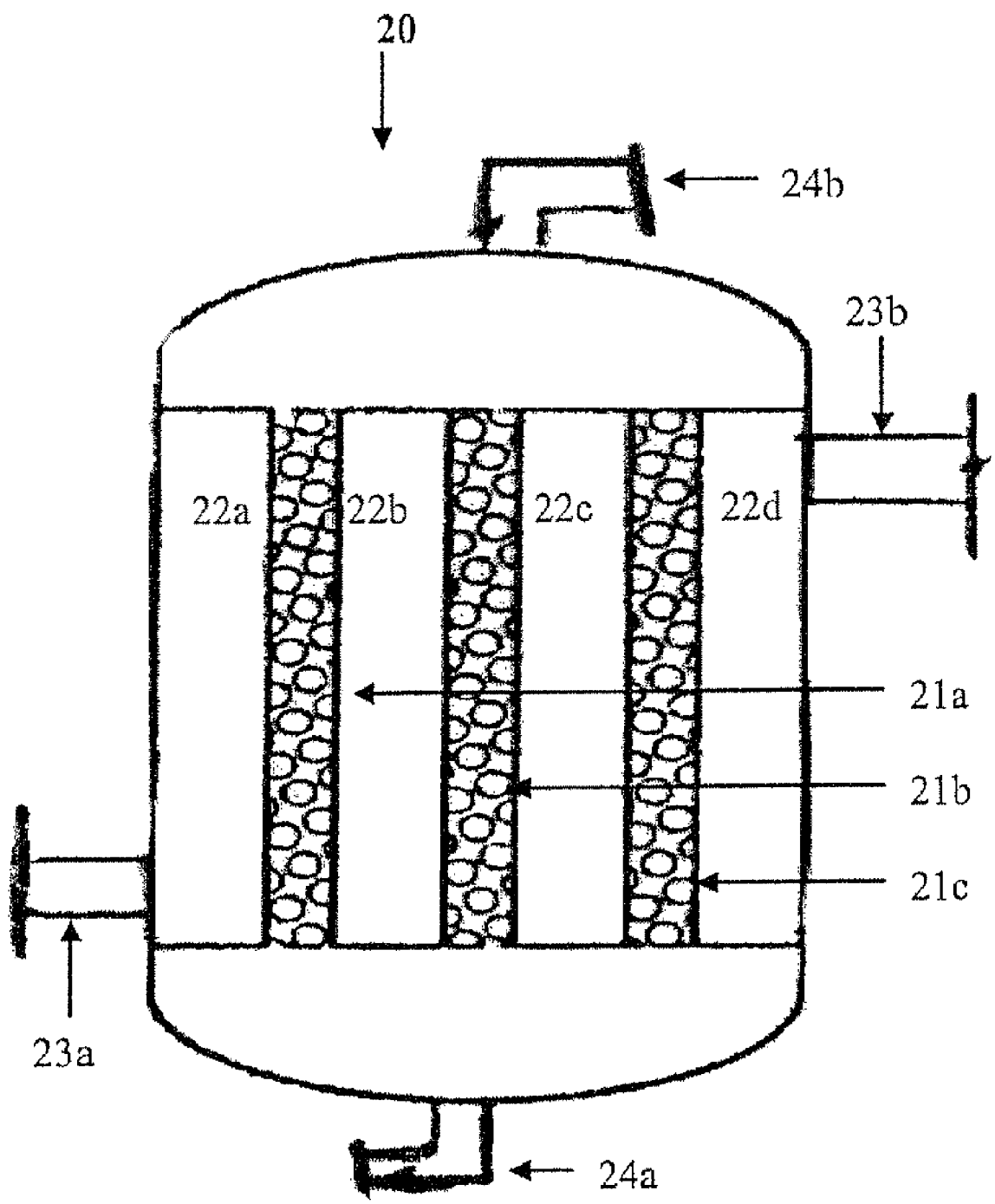
FIG. 2 schematically depicts an embodiment of the apparatus of the present invention that includes tubular reaction chambers and thermal-transfer chambers.

FIG. 2 schematically depicts one embodiment of the current invention wherein the reaction chambers are tubular in shape. The apparatus 20 includes three substantially similar tubular reaction chambers 21a, 21b, and 21c. Also present is a feed inlet, 24a, for the introduction of wet ethanol, and a product outlet, 24b, for the removal of dry ethanol. Each reaction chamber further includes a particulate bed including sorbent particles or a mixture of sorbent particles and catalyst particles. The apparatus 20 includes four thermal-transfer chambers, 22a, 22b, 22e, and 22d. Also present is an inlet port, 23a for the introduction of a heating or cooling agent and an outlet port, 23b, for removal of the heating or cooling agent. In further embodiments of the invention, the apparatus may contain four, five, or more reaction chambers. Likewise the apparatus may contain five, six, or more thermal-transfer chambers. In another embodiment, each reaction chamber and each thermal-transfer chamber in the apparatus may be provided with individual inlet and outlet ports.

In one embodiment, the present invention employs a configuration that comprises a combination of non-adiabatic and adiabatic portions. In the non-adiabatic part of the bed, a fine sorbent, that is an absorbent of small particle size, is packed in the reaction chambers of a tubular reactor. Desirably the particle size is in the range of about 0.01 cm to 0.25 cm and suitably in the range of about 0.10 cm to 0.20 cm.

Small sorbent materials are often more effective than large materials for the absorption of water because of their higher surface area. However, their reaction with water is generally a very exothermic process and excess heat will be generated. Sorbents that are very small particles will also be characterized by relatively rapid heat transfer. In an adiabatic adsorption column, a fine sorbent cannot usually be used in the inlet part because the generated heat would result in very high temperatures. Consequently, the sorbent material would suffer thermal damage caused by sintering at these elevated temperatures.

In a tubular reactor, uptake of water by the fine sorbent occurs rapidly, but the thermal-transfer chamber can be used to cool the reaction chamber by removing the liberated heat. For example, low-pressure steam can be used in the thermal-transfer chamber for cooling. The steam is used in conjunction with an external heat-exchanger. Thus, the reaction chamber and the sorbent particles operate quasi-isothermally. Following the non-adiabatic portion is an adiabatic portion where the final adsorption step occurs. This portion is also packed with fine sorbent material and operates as a guard bed to ensure that water removal occurs to an adequate degree and that the final ethanol is sufficiently dry. Because water removal occurs much faster with fine particles and also because of a high pressure drop, the bed of fine sorbent particles in the adiabatic portion can be relatively short, saving sorbent and lowering the unit cost.

In order to regenerate the fine sorbent from the hydrated-sorbent, it is necessary to heat the hydrated-sorbent to remove the water. The hydrated-sorbent in the reaction chamber can be heated by introducing a hot material, such as high-pressure steam, into the adjacent thermal-transfer chamber. A useful heating method includes the use of steam in conjunction with an external heat-exchanger.

It is possible to use the thermal-transfer chamber of a tubular reactor for simultaneous cooling of sorbent in one adjacent reaction chamber and heating of hydrated-sorbent in another adjacent reaction chamber. The heat generated by the reaction of water and sorbent in one chamber is transferred via the thermal-transfer chamber to a reaction chamber containing hydrated-sorbent. The transferred heat assists in removing water from the hydrated-sorbent and regenerating sorbent.

Adiabatic systems, such as the one described above, are difficult to heat for two reasons: first, the thermal capacity of the solid is three orders of magnitude higher than the thermal capacity of gas, and second, the heat transfer from the thermal-transfer chamber in a radial direction through the adsorbent material is slow. Alternative means of heating are therefore required that can be utilized in a large scale process in an economical manner.

The method of heating the sorbent by a chemical reaction, such as by mixing of sorbent particles and catalyst particles and introducing a fuel to the reactor, has been described previously. This method can also be employed advantageously in a tubular reactor. For example, the fine-particle sorbent may be mixed with catalyst particles in the same manner as described previously. After the fine-particle sorbent removes water from ethanol, becomes hydrated, and the dry ethanol is removed, a fuel can be introduced into the tubular reaction chamber. In the presence of the catalyst, the fuel reacts, for example, with water, and generates heat. At the same time, it is optionally possible to introduce a hot material, such as high-pressure steam, into the thermal-transfer chamber(s). Thus the hydrated-sorbent is heated and the sorbent is regenerated and the resulting water vapor is removed. At this point it may be desirable to cool the sorbent. This can be accomplished in several ways, including the "cold shot" procedure described previously. It is also feasible to introduce a cold material, such as low-pressure steam, into the thermal-transfer chamber(s) resulting in cooling of the sorbent material by heat transfer.

In a further aspect of the invention, the inventive apparatus includes a reaction chamber for foaling a slurry of ethanol and sorbent, including an inlet port for adding wet ethanol, an inlet port for adding sorbent particles, and an exit port for removing a slurry of dry ethanol and hydrated-sorbent particles. The apparatus includes a separator for separating hydrated-sorbent from dry ethanol and a means for transporting the hydrated-sorbent and ethanol mixture from the reaction chamber to the separator. The apparatus also includes a fluidization unit and a means for transporting the hydrated-sorbent from the separator to the fluidization unit. In the fluidization unit, the hydrated-sorbent can be dried to regenerate the sorbent. For example, the hydrated-sorbent can be treated with hot air in the fluidization unit to remove water. The heated and regenerated sorbent can be cooled by treatment with ethanol. Vaporization of the ethanol cools the sorbent. The apparatus includes a means of returning the regenerated sorbent to the reaction chamber. A useful means of transporting ethanol, and mixtures of ethanol and sorbent is by pumping the material through pipes or tubing.

Useful materials for sorbent particles have been described previously. The sorbent particles desirably have a size in the range of about 0.01 to 0.50 cm and suitably in the range of about 0.05 to 0.35 cm.

Figure 3:
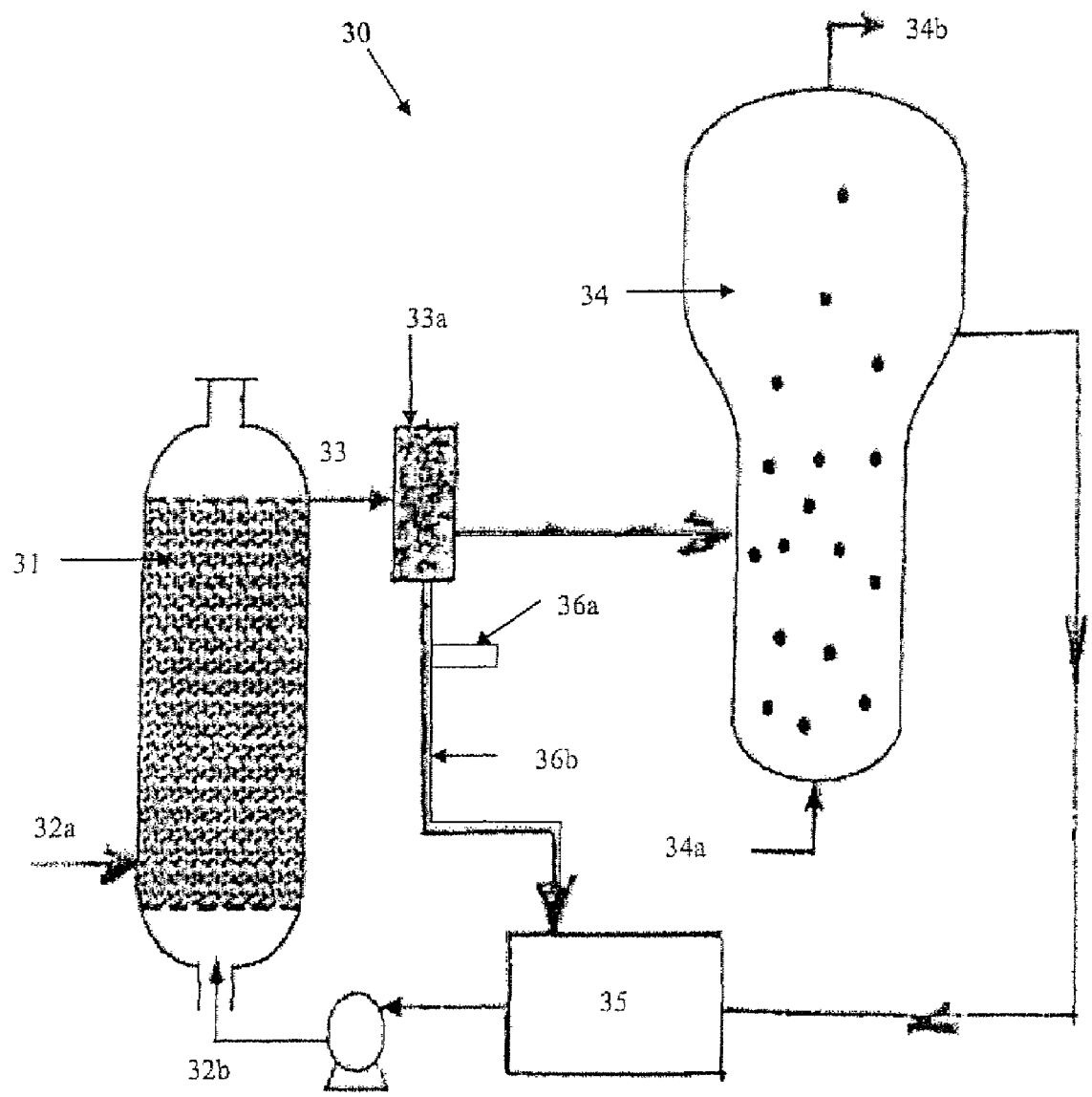
FIG. 3 schematically depicts an embodiment of the apparatus of the present invention that includes a slurry reaction chamber.

FIG. 3 schematically depicts one embodiment of the current invention. The apparatus, 30, includes a slurry unit, 31, wherein a mixture of sorbent and wet ethanol are combined. The slurry unit also includes an inlet port, 32a, for adding wet ethanol, an inlet port, 32b, for adding sorbent, and an exit port, 33, for removing a mixture of dry ethanol and hydrated-sorbent. In some embodiments, the slurry unit may also contain a means of agitating the mixture of sorbent and ethanol, such a stirrer including a propeller and a motor for rotating the propeller. The wet ethanol and the sorbent are introduced into the slurry unit, 31, a slurry is formed and water is transferred from the wet ethanol to the sorbent. The dry ethanol and hydrated-sorbent exit the slurry unit and the mixture is transported to the separator unit, 33a. The separator includes a means of separating the dry ethanol from the hydrated-sorbent, such as, for example, a filter.

The hydrated-sorbent that has been separated is transported to the fluidized dryer, 34. In the fluidized dryer, hot air enters by means of inlet 34a and heats the hydrated-sorbent releasing the water as vapor. The air and water vapor exit through the outlet port, 34b. The dried hot sorbent is then transported to the mixing unit 35, which includes a heat exchanger, which is used to cool the sorbent. After cooling, the sorbent is then returned to the reaction chamber, 31 by means of inlet port, 32b.

The dry ethanol is removed by transfer line, 36a. A portion of the dry ethanol from the separator unit, 33a, may be transported to the mixer unit, 35, by means of the transfer line, 36b. This portion of ethanol is also used to cool the hot sorbent.

Useful means of transporting materials between units of the apparatus include pumping ethanol or mixtures of ethanol and sorbent, as well as pneumatically moving sorbent and mixtures of sorbent and gaseous ethanol.

In a still further aspect of the invention, the inventive apparatus includes a reaction chamber including an inlet port for wet ethanol in the gas state, an inlet port for adding small sorbent particles, and an exit port for removing a mixture of hydrated-sorbent particles and dry ethanol in the gas state. The apparatus includes a cyclone separator, that is, a device that separates materials by centrifugal force, and a means of transporting the mixture of gaseous ethanol and hydrated-sorbent particles from the reactor to the cyclone separator. The cyclone separator acts to separate the hydrated-sorbent particles from the dry ethanol and to condense the gaseous ethanol to liquid dry ethanol. The cyclone separator includes a means to collect the dry ethanol. The apparatus includes a means to transport the hydrated-sorbent separated in the cyclone separator to a fluidized bed. The fluidized bed is heated by an imbedded heat exchanger. Water is removed from the hydrated-sorbent entering the heated fluidized bed and the sorbent is regenerated. The apparatus includes a means to cool the regenerated sorbent and transport said sorbent to the reaction chamber.

Useful materials for sorbent particles have been described previously. The sorbent particles desirably have a size in the range of about 0.01 to 0.75 cm and suitably in the range of about 0.05 to 0.50 cm.

A useful means of transporting small particles includes a pneumatic device, that is, by using a tube or pipe and a stream of compressed gas such as compressed air.

Figure 4:
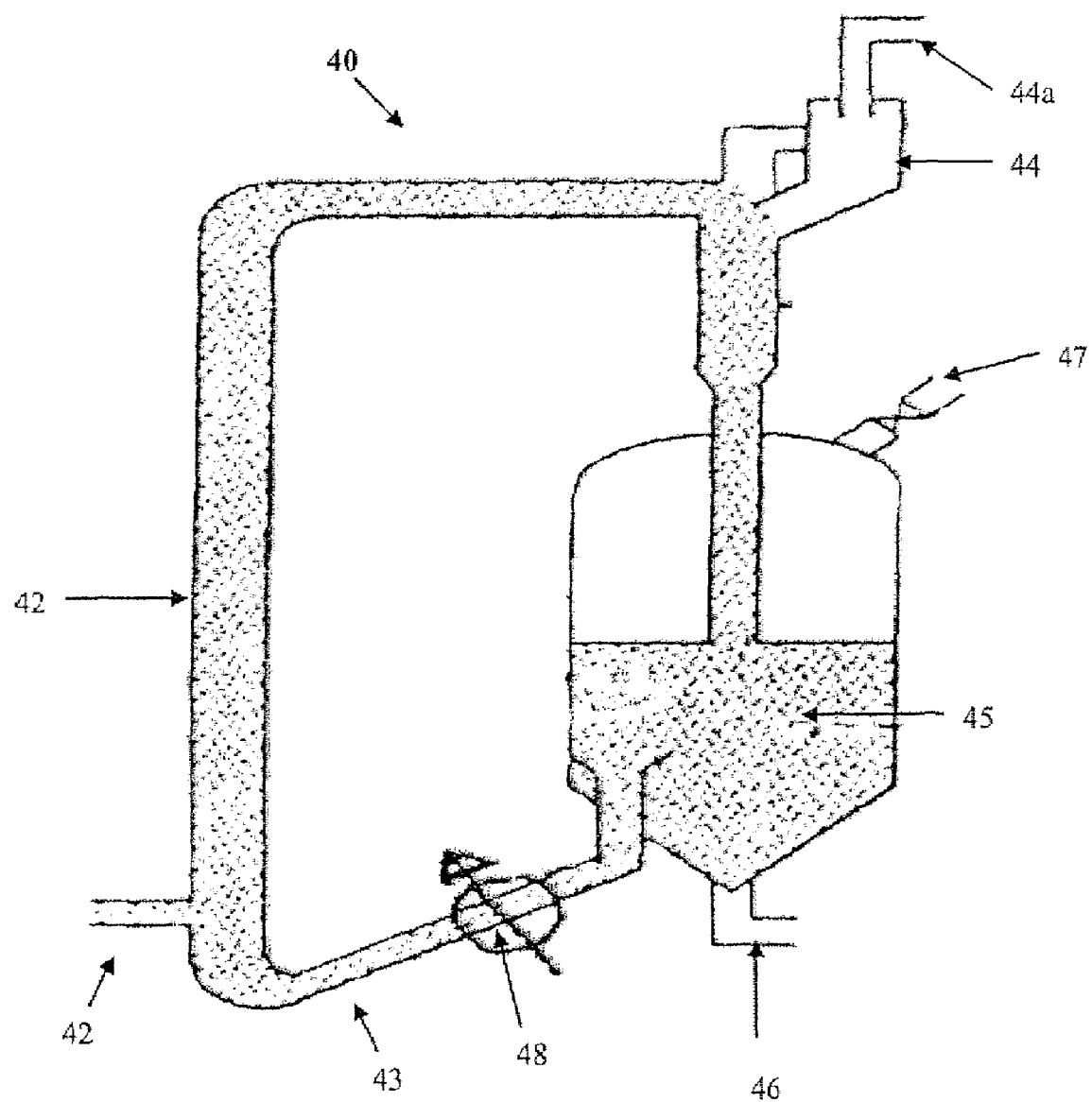
FIG. 4 schematically depicts an embodiment of the apparatus of the present invention that includes a transfer-line reaction chamber and a pneumatic transport system.

FIG. 4 schematically depicts one embodiment of the current invention. The apparatus 40, includes a transfer-line reactor, 41. Wet ethanol in the gas state, that is a mixture of ethanol vapor and water vapor, enters the reactor by means of inlet port 42. Sorbent particles enter the reactor by means of transfer line 43. The wet gaseous ethanol and the sorbent particles are mixed in the transfer-line reactor, 41. Mixing occurs while the materials are transported to a cyclone separator unit, 44, and the sorbent particles remove the water from the ethanol. At the cyclone separator unit, the hydrated-sorbent particles are separated from the dry gaseous ethanol.

The dry gaseous ethanol is transported to a condenser unit by means of transfer line 44a, wherein the gaseous ethanol is condensed to liquid dry ethanol, which is collected.

The hydrated-sorbent is transported to a fluidized bed unit, 45. The fluidized bed is heated by an imbedded heat exchanger. Hot air enters the unit by means of inlet port, 46. The sorbent is heated by the hot air and water is removed from the hydrated-sorbent, regenerating the sorbent. The water vapor formed and the cooler air present exit the unit by means of outlet port, 47. The regenerated hot sorbent is transported to a cooling unit, 48. The cooling unit acts on the hot sorbent by means of a heat exchanger. It may also be useful to treat the hot sorbent with liquid ethanol to provide additional cooling. After cooling, the sorbent is returned to the transfer-line reactor, 41, by means of transfer line 43.

Another aspect of the present invention is directed toward a process for drying ethanol. This process has several embodiments, which have been described previously. One embodiment comprises introducing a feed of wet ethanol via a feed inlet 12a, 12b into a first reaction chamber 11a, 11b. Desirably wet ethanol includes less than 80% water, suitably less than 70% water and preferably less than 50% water. The first reaction chamber contains a particulate bed comprising sorbent particles. Preferred sorbent particles have been described previously. Water from the wet ethanol is taken-up by the sorbent particles. Dry ethanol is removed from the reaction chamber via the product outlet 13a, 13b. Desirably the dry ethanol contains less than 1% by weight of water, preferably less than 0.5% water, and more preferably 0.3% or less of water.

The particulate bed 14a, 14b comprises a first zone 14a-1, 14b-1 proximate the feed inlet 12a, 12b, respectively, and a second zone 14b-1, 14b-2 proximate the product outlet 13a, 13b, respectively, the sorbent particles in the first zone having an average particle size larger than the average particle size of the sorbent particles in the second zone. Preferably, the sorbent and catalyst particles in the first zone have an average particle size in the range of about 0.15 to 0.75 cm and desirably a particle size of approximately 0.32 cm (0.125 inch) diameter. Preferably, the sorbent and catalyst particles in the second zone have an average particle size in the range of about 0.05 to 0.25 cm and desirably an average particle size of approximately 0.16 cm (0.061 inch) diameter.

The process of the invention may further comprise heating the sorbent particles to effect removal of adsorbed water from the sorbent particles, followed by cooling the heated sorbent particles. In one embodiment, heating of the sorbent particles is achieved by introducing a fuel into the reaction chamber via fuel inlets 15a, 15b. The fuel reacts with materials present in the reactor, for example, with water, and thereby generating heat. Heat generating reactions are promoted by inclusion of catalyst particles in the particulate bed within the reaction chamber. Preferably, the sorbent and catalyst particles are present in the particulate bed in a weight ratio of about 10:1 to about 30:1 sorbent:catalyst.

In accordance with the present invention, the process for drying ethanol may comprise a PSA process, wherein regeneration of the adsorbent is commenced before the heat pulse generated by water adsorption has reached the downstream end of the particulate bed. Alternatively, the process may comprise a TSA process wherein the heat pulse generated by water adsorption exits the downstream end of the particulate bed during the wet alcohol feed, thereby requiring introduction into the chamber of a fuel that undergoes combustion promoted by an oxidation catalyst included in the particulate bed. In addition, the process of the invention may be a combined PSA-TSA process wherein sorbent regeneration is achieved by a combination of reverse flow of hot gas and combustion of introduced fuel in the reaction chamber.

As described previously, in one phase of operation, the sorbent particles operate to remove water from the wet ethanol to form hydrated-sorbent particles. The adsorption of water on solid adsorbents is an often strongly exothermic reaction; consequently a large amount of heat is frequently liberated. As the temperature of the solid adsorbent increases, the adsorptive efficiency of the hot solid phase may be diminished, and the capacity of the bed consequently may be reduced. To cope with this situation, it is often desirable to keep the bed close to isothermal conditions.

In one embodiment, isothermal conditions may be achieved by, for example, providing the adiabatic adsorption bed with "cold shot," injected into the bed, preferably in the liquid state, at different positions in the axial direction. For example, in FIG. 1, the apparatus 10 provides for coolant inlets 16a and 16b, respectively, for the introduction of coolant to cool particulate beds 14a and 14b, respectively. Desirably the cold shots include injection of a liquid such as ethanol or ethanol/water mixture into the reaction bed containing hot absorbent. This will result in rapid evaporation of the liquid, which will dissipate thermal energy, and aid in keeping the sorbent at quasi-isothermal conditions.

The apparatus and methods described above may also be applied to the drying of alcohols other than ethanol. In particular, the apparatus and methods described may be used to remove water from wet 1-butanol.

Embodiments of the current invention may provide reduced costs, greater productivity, higher efficiency, as well as ease of manufacturing.

While the invention has been described by reference to various specific embodiments, it should be understood that numerous changes may be made within the spirit and scope of the inventive concepts described. Accordingly, it should be recognized that the invention is not limited to the described embodiments but has full scope defined by the language of the following claims.

PARTS LIST

10 Apparatus
11a Wet Ethanol Inlet
11b Wet Ethanol Inlet
12a Reaction Chamber
12b Reaction Chamber
13a Dry Ethanol Outlet
13b Dry Ethanol Outlet
14a Particulate Bed
14b Particulate Bed
14a-1 First Zone
14a-2 Second Zone
14b-1 First Zone
14b-2 Second Zone
15a Gas Inlet
15b Gas Inlet
16a Coolant Inlet
16b Coolant Inlet
17a Gas Outlet
17b Gas Outlet
V Valve
20 Tubular Reactor Apparatus
21a Tubular Reactor Chamber
21b Tubular Reactor Chamber
21c Tubular Reactor Chamber
22a Thermal-Transfer Chamber
22b Thermal-Transfer Chamber
22c Thermal-Transfer Chamber
22d Thermal-Transfer Chamber
23a Inlet Port
23b Outlet Port
24a Inlet Port
24b Outlet Port
34 Slurry Reactor Apparatus
31 Slurry Reactor Chamber
32a Inlet Port
32b Inlet Port
33 Outlet Port
33a Separator Unit
34 Dryer Unit
34a Inlet Port
34b Outlet Port
35 Mixer Unit
36a Transfer Line
40 Transfer-Line Reactor Apparatus 41 Transfer-Line Reactor Chamber
42 Inlet Port
43 Transfer line
44 Separator Unit
44a Transfer Line
45 Fluidized Bed
46 Inlet Port
47 Outlet Port
48 Cooling Unit

The invention claimed is:

1. A process for drying ethanol comprising the steps of:
   a. introducing wet ethanol through a feed inlet into a first reaction chamber, said first reaction chamber further including a product outlet for removing dry ethanol from said reaction chamber;
   b. providing a particulate bed of sorbent particles within said first reaction chamber, said particulate bed including a first zone proximate said teed inlet and a second zone proximate said product outlet, said sorbent particles in said first zone having an average particle size larger than the average particle size of said sorbent particles in said second zone, said particulate bed of sorbent particles further including particles of a catalyst effective for generating a heat-generating reaction;
   c. adsorbing water from said wet ethanol onto said sorbent particles and forming hydrated-sorbent particles; and
   d. removing dry ethanol from said reaction chamber via said product outlet.

2. The process of claim 1 and further comprising:
   a. heating said hydrated-sorbent particles and thereby causing removal of adsorbed water from said hydrated-sorbent particles and thereby regenerating said sorbent particles; and
   b. cooling said heated sorbent particles following removal of said adsorbed water from said hydrated-sorbent particles.

3. The process of claim 1 wherein said reaction chamber further comprises a coolant inlet for introducing a coolant into said reaction chamber, and wherein, said cooling of said heated sorbent particles comprises introducing a coolant into said reaction chamber.

4. The process of claim 1 wherein said reaction chamber further comprises a fuel inlet for introducing a fuel into said reaction chamber, and said particulate bed disposed within said first reaction chamber further comprises catalyst particles, and wherein:
   a. said heating of said sorbent particles comprises oxidizing said fuel or reducing said water in the presence of said catalyst, thereby generating heat.

5. The process of claim 4 wherein said catalyst particles comprise an oxidation catalyst, a water-gas shift catalyst or a combination thereof 6. The process of claim 5 wherein said oxidation catalyst comprises platinum-activated alumina.

7. The process of claim 4 wherein said catalyst is a water-gas shift catalyst comprising a copper oxide, a zinc oxide, or aluminum oxide.

8. The process of claim 1 wherein said sorbent particles comprise alumina, silica, or zeolite.

9. The process of claim 1 wherein said sorbent particles and said catalyst particles are present in said particulate bed in a weight ratio of about 10:1 to about 30:1 sorbent: catalyst.

10. The process of claim 1 wherein said sorbent particles and said catalyst particles in said first zone have an average particle size of approximately 0.32 cm diameter, and said sorbent particles and said catalyst particles in said second zone have an average particle size of approximately 0.16 cm diameter.

11. The process of claim 4 wherein said fuel comprises carbon monoxide.

12. The process of claim 2 wherein said heated sorbent particles are cooled by mixing with liquid ethanol.

13. The process of claim 1 and further comprising the steps of:
   a. heating said hydrated-sorbent particles in said first reaction chamber thereby causing removal of water and thereby regenerating said sorbent particles;
   b. cooling said heated sorbent particles in said first reaction chamber following removal of said water from said hydrated-sorbent particles;
   c. introducing wet ethanol into a second reaction chamber substantially similar to said first reaction chamber;
   d. adsorbing water from said wet ethanol onto sorbent particles in said second reaction chamber; and
   e. removing dry ethanol from said second reaction chamber.

14. The process of claim 1 wherein said particles in said first zone are approximately 0.32 cm in diameter.

15. The process of claim 1 wherein said particles in said second zone are approximately 0.16 cm in diameter.

16. The process of claim 1 wherein said particles in said first zone are approximately 0.32 cm in diameter and said particles in said second zone are approximately 0.16 cm in diameter.

17. The process of claim 1 and further comprising the step of regenerating said sorbent particles using a TSA process.

18. The process of claim 1 and further comprising the step of regenerating said sorbent particles using a PSA process.

19. The process of claim 1 and further comprising the step of regenerating said sorbent particles using a combined PSA and TSA process.

20. The process of claim 1 wherein the wet ethanol is prepared by a fermentation process or by a process comprising the hydration of ethylene.

21. The process of claim 1 wherein the dry ethanol product comprises no more than 0.3% water by weight.

* * * * *